United States Patent
Hernandez-Castaneda et al.

(10) Patent No.: US 11,278,200 B2
(45) Date of Patent: Mar. 22, 2022

(54) MEASUREMENT METHOD FOR THE DETERMINATION OF A VALUE OF A VISUAL CORRECTION NEED FOR NEAR VISION OF AN INDIVIDUAL

(71) Applicant: Essilor International, Charenton-le-Pont (FR)

(72) Inventors: Martha Hernandez-Castaneda, Charenton-le-Pont (FR); Konogan Baranton, Charenton-le-Pont (FR); John Carrier, Charenton-le-Pont (FR)

(73) Assignee: Essilor International, Charenton-le-Pont (FR)

( * ) Notice: Subject to any disclaimer, the term of this patent is extended or adjusted under 35 U.S.C. 154(b) by 350 days.

(21) Appl. No.: 16/333,424

(22) PCT Filed: Sep. 14, 2017

(86) PCT No.: PCT/EP2017/073198
§ 371 (c)(1),
(2) Date: Mar. 14, 2019

(87) PCT Pub. No.: WO2018/050778
PCT Pub. Date: Mar. 22, 2018

(65) Prior Publication Data
US 2019/0246896 A1     Aug. 15, 2019

(30) Foreign Application Priority Data
Sep. 15, 2016   (EP) .................................. 16306180

(51) Int. Cl.
*A61B 3/09*     (2006.01)
*A61B 3/028*    (2006.01)
(Continued)

(52) U.S. Cl.
CPC .............. *A61B 3/09* (2013.01); *A61B 3/0025* (2013.01); *A61B 3/0033* (2013.01);
(Continued)

(58) Field of Classification Search
CPC ................................. A61B 3/028; A61B 3/09
(Continued)

(56) References Cited

U.S. PATENT DOCUMENTS 2,523,007 A    9/1950  Glazer
4,778,268 A *  10/1988 Randle .................... A61B 3/09
                                                351/203
(Continued)

FOREIGN PATENT DOCUMENTS

CN        1520270 A     8/2004
CN      101396259 A     4/2009
(Continued)

OTHER PUBLICATIONS

International Search Report, dated Nov. 24, 2017 from corresponding PCT/EP2017/073198 application.
(Continued)

*Primary Examiner* — Zachary W Wilkes
(74) *Attorney, Agent, or Firm* — Nixon & Vanderhye

(57) ABSTRACT

Disclosed is a measurement method for determining a value of a visual correction need for near vision of an individual in a natural posture for near vision. A recognizing limit distance is determined so that the individual is able to recognize at least one predetermined symbol farther than the limit distance relatively to the individual and unable to recognize the at least one predetermined symbol closer to the individual than the limit distance. A portable medium displaying the predetermined symbol is displaced in front of the face and eyes of the individual to change a frontal distance between his/her eyes and the portable medium and
(Continued)

in which when a recognizing limit distance is detected by the individual, the limit distance is measured and the value of the visual correction need is determined from the measured limit distance, wherein the visual correction need includes an accommodation compensation need.

14 Claims, 1 Drawing Sheet

(51) Int. Cl.
    *A61B 3/00*         (2006.01)
    *A61B 3/032*       (2006.01)
    *A61B 3/11*         (2006.01)

(52) U.S. Cl.
    CPC ............ *A61B 3/0041* (2013.01); *A61B 3/028* (2013.01); *A61B 3/0325* (2013.01); *A61B 3/111* (2013.01); *A61B 2560/0223* (2013.01); *A61B 2560/0431* (2013.01)

(58) Field of Classification Search
    USPC .......................................................... 351/239
    See application file for complete search history.

(56) References Cited

U.S. PATENT DOCUMENTS

| | | | | |
|---|---|---|---|---|
| 5,929,971 | A * | 7/1999 | Hosoi | .................. A61B 3/0285 351/237 |
| 7,341,350 | B1 | 3/2008 | Kadambi | |
| 7,374,285 | B2 | 5/2008 | Toshima et al. | |
| 8,262,225 | B2 * | 9/2012 | Ueno | .................. A61B 3/1035 351/239 |
| 8,820,931 | B2 * | 9/2014 | Walsh | .................. A61B 5/0073 351/206 |
| 9,039,182 | B2 * | 5/2015 | Huang | ..................... G06K 9/46 351/239 |
| 9,223,151 | B2 | 12/2015 | Haddadi et al. | |
| 9,468,370 | B1 * | 10/2016 | Shearer | ..................... A61B 3/09 |
| 2006/0078858 | A1 * | 4/2006 | Vroman | ................... A61B 5/16 434/179 |
| 2006/0152675 | A1 | 7/2006 | Toshima et al. | |
| 2013/0301007 | A1 * | 11/2013 | Wolffsohn | ............... A61B 3/09 351/239 |
| 2016/0120402 | A1 | 5/2016 | Limon | |
| 2016/0140692 | A1 | 5/2016 | Pais et al. | |

FOREIGN PATENT DOCUMENTS

| | | | |
|---|---|---|---|
| CN | 103517666 A | 1/2014 | |
| CN | 105764405 A | 7/2016 | |
| DE | 3912806 A1 * | 1/1990 | ............... A61B 3/09 |
| JP | 2007 097707 A | 4/2007 | |
| JP | 2007097707 A * | 4/2007 | |
| WO | 2014/195951 A1 | 12/2014 | |

OTHER PUBLICATIONS

Office Action issued in Chinese Patent Application No. 201780056422.2 dated Feb. 3, 2021.

* cited by examiner

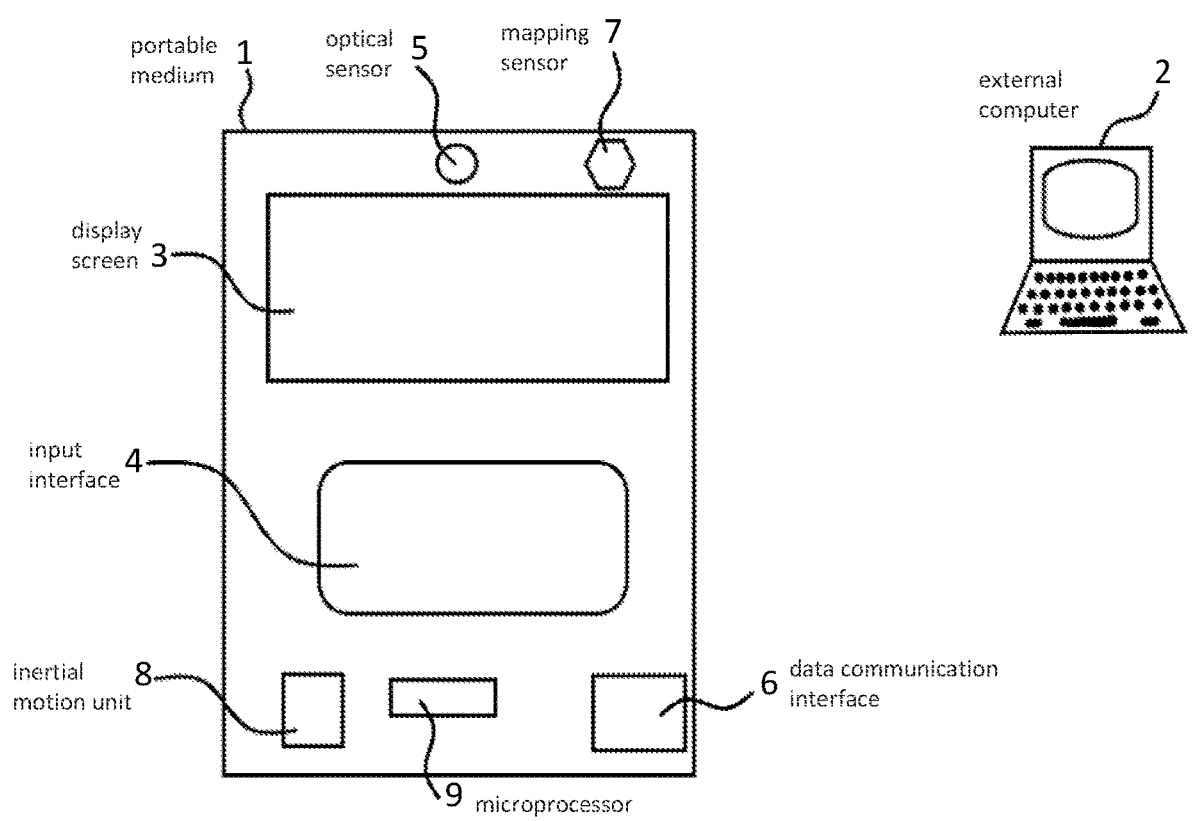

MEASUREMENT METHOD FOR THE DETERMINATION OF A VALUE OF A VISUAL CORRECTION NEED FOR NEAR VISION OF AN INDIVIDUAL

TECHNICAL FIELD OF THE INVENTION

The present invention is related to a measurement method for the determination of a value of a visual correction need for the near vision of an individual. In particular, the measurement method allows the computation of the visual correction need for near vision as an additional correction to an eventual correction for far vision. That additional correction is called ADDITION. The method uses a smartphone, a tablet or any other relevant electronic device. It can be used for an individual having far vision impairment that is already corrected with a pair of glasses or any other equivalent means.

BACKGROUND INFORMATION AND PRIOR ART

In many instances, notably in countries with few eye care resources, the professionals that may provide correction to people having impaired vision and in particular impaired near vision, do not have access to sophisticated equipments able to measure the level of needed correction or do not know well the methods used to compute the correction need and specifically the ADDITION for the correction of the near vision. Said ADDITION is notably used for the fabrication of bifocal lenses or progressive lenses. This results in people not having proper correction for near vision and thus discomfort and visual fatigue.

Various solutions have been proposed in the field of near or far vision corrections. In document US 2016/0140692 it is disclosed a "Systems and methods for configuring the display resolution of an electronic device based on distance and user presbyopia" that may use magnified images of the eye that are analyzed. In document US20060152675, the disclosure is about a "Method measurement of eye without prescription" but it prove to be more complex in the case of astigmatism or for a high myopic because in these cases the distance measurement must be more precise to give a proper correction. Moreover, the positioning relative to the computer screen is not using a reading task. The document WO2014/195951 is related to a "Method of measure with the objective to estimate the refraction in far vision".

A goal of the current invention is to improve the measurement method in the determination of the correction need for near vision, in particular the determination of ADDITION, with simple tools and giving accurate results. The measurement method is adapted to be included in an electronic device, typically a smartphone, and may be used by any person involved in the correction of vision impairments or even the individual needing such a correction, specifically in near vision. It may also be used solely by individuals needing a correction for near vision through the use of a telephone or computer network allowing them to determine their needs and order through the network a pair of glasses with the determined correction.

SUMMARY OF THE INVENTION

With reference to the drawing FIGURE, the current invention is related to a measurement method for determining a value of a visual correction need for near vision of an individual in a natural posture for near vision, in which a recognizing limit distance is determined so that the individual is able to recognize at least one predetermined symbol disposed farther than said limit distance relatively to the individual and unable to recognize said at least one predetermined symbol disposed closer to the individual than said limit distance, and a portable medium 1 displaying said at least one predetermined symbol is displaced in front of the face and eyes of the individual to change a frontal distance between his/her eyes and the portable medium 1 and in which when a recognizing limit distance is detected by the individual, said limit distance is measured and the value of the visual correction need is determined from said measured limit distance.

According to the invention, the visual correction need comprises an accommodation compensation need.

It has to be noted that the wording "recognize" should be understood in a general way of recognizing a visual element, in particular as having a meaning or some particular characteristics, for example by being able to read a text, by being able to assess the contrast between two predetermined symbols . . . .

The following embodiments that can be used alone or according to any technical combination are also considered:
  the portable medium 1 is an electronic device comprising
    at least a display screen 3, a mapping sensor 7 and an input interface 4, designed to ensure that:
    the display screen 3 displays the at least one predetermined symbol, and
    when the input interface 4 receives from the individual an entry corresponding to the detection by the individual of the limit distance, the distance between the face, preferably the eyes, of the individual and the electronic device obtained from the mapping sensor 7 is kept as being the measured limit distance and said distance being used to compute the value of the visual correction,
  the mapping sensor 7 is selected from an ultrasonic sensor capable of measuring distances, an optical sensor 5 capable of measuring distances, a moiré optical sensor capable of measuring distances, a scanning light beam sensor capable of measuring distances, a 3D camera capable of measuring distances,
  the portable medium 1 is an electronic device comprising
    at least a display screen 3, an optical sensor 5 and an input interface 4, designed to ensure that:
    the display screen 3 displays the at least one predetermined symbol,
    the optical sensor 5 records images of the face of the individual, at least while the distance between his/her eyes and the electronic device changes,
    the distance between the eyes of the individual and the electronic device is computed from the images, and
    when the input interface 4 receives from the individual an entry corresponding to the detection by the individual of the limit distance, the corresponding computed distance is kept as being the measured limit distance, said corresponding computed distance being used to compute the value of the visual correction,
  the portable medium 1 is an electronic device further comprising computation circuits with a microprocessor 9 executing a program, the portable medium 1 being designed to ensure that at least the value of the visual correction is computed by the computation circuits within the portable medium 1,
  the electronic device is connected through a network to an external computer 2 or server, the portable medium 1 is an electronic device further comprising a data communication interface 6 for exchanging data to and from an external computer 2, the portable medium 1 and the external computer 2 being designed to ensure that at least the value of the visual correction is computed by the external computer 2, the external computer 2 is a local computer, the external computer 2 is a remote computer, the data communication interface 6 is selected from telephone wired or radio (i.e. GSM . . . ), RNIS, TCP/IP, WIFI®, BLUETOOTH®, or equivalent, the electronic device is a smartphone or a tablet or a portable computer, the portable medium 1 and the external computer 2 being designed to ensure that the distance between the eyes of the individual and the electronic device is computed by the external computer 2, the portable medium 1 is an electronic device comprising at least a display screen 3, an optical sensor 5, an input interface 4 and computation circuits with a microprocessor 9 executing a program, designed to ensure that:

the display screen 3 displays the at least one predetermined symbol, the optical sensor 5 records images of the face of the individual, at least while the distance between his/her eyes and the electronic device changes, the computation circuits computes from the recorded images the distance between the eyes of the individual and the electronic device and when the input interface 4 receives from the individual an entry corresponding to the detection by the individual of the limit distance, the computation circuits keeps the corresponding computed distance as being the measured limit distance, said corresponding computed distance being used by the computation circuits to compute the value of the visual correction, the individual has an impaired far vision and the individual is wearing a pair of glasses correcting his/her impaired far vision during the measurement method for the determination of the value of the visual correction need for near vision, the individual has a perfect far vision and the individual is not wearing a pair of glasses, in an initial step of the method, before the electronic device is displaced to change the distance between the eyes and the electronic device, the electronic device is calibrated to determine the projection ratio F in degrees per pixel, and, in case the electronic device further comprises an inertial motion unit 8 for recording motions of the electronic device, the determination of the projection ratio F is done by oscillating with rotation the electronic device and computation of recorded motions with reference to the recorded related images to quantify the displacement P in pixels of an object in the recorded images and the corresponding angular rotation A of said object, F being computed with $F=A/P$, the object in the recorded images is an object located at a far distance from the electronic device, preferably at 5 m or more, in an initial step of the method, before the electronic device is displaced to change the distance between the eyes and the electronic device, the electronic device is calibrated to determine the projection ratio F in degrees per pixel using a reference object of know size that is arranged to be imaged in the recorded images, the reference object is arranged at a predefined known distance of the electronic device during the initial step of calibration, the reference object has scale marks of length and the size of the reference object is determined by the electronic device, the electronic device determines the size of the reference object by analyzing at least an image of the reference object, in a next initial step of the method, before the electronic device is displaced to change the distance between the eyes and the electronic device, the electronic device is located at a predefined distance from the face and eyes of the individual and the electronic device is configured to display sets of the at least one predetermined symbol, each set having a predefined size and thus predefined angular size given the predefined distance of location, and the individual selects the recognizable set of size just above the one he/she is unable to recognize, and said selected size or angular size is used throughout the following steps of the method of determination of the value of the visual correction need for near vision, in a next initial step of the method, before the electronic device is displaced to change the distance between the eyes and the electronic device, the electronic device is hold by the individual farthest as possible to his/her face and the electronic device is configured to display sets of the at least one predetermined symbol, each set having a predefined size, and the individual selects the recognizable set of size just above the one he/she is unable to recognize, and said selected size is used throughout the following steps of the method determination of the value of the visual correction need for near vision, in a next initial step of the method, before the electronic device is displaced to change the distance between the eyes and the electronic device, the electronic device is hold by the individual farthest as possible to his/her face and the electronic device is configured to display sets of the at least one predetermined symbol, each set having a predefined size, and the individual selects the recognizable set of size just above the one he/she is unable to recognize, and the electronic device is configured to compute the distance between the eyes and the electronic device and to compute the related angular size for the at least one predetermined symbol of the selected set and said related angular size is used throughout the following steps of the method determination of the value of the visual correction need for near vision, in the method, the individual holds by his/her hand the electronic device displaying said at least one predetermined symbol and said individual displaces the electronic device in front of his/her face and eyes to change a frontal distance between his/her eyes and the electronic device and when the limit distance is detected by the individual, said limit distance is measured, the displacements of the electronic device are obtained by the stretching or folding of the upper limb by the individual, in the method, the electronic device is not hold by the individual but, instead, by an assistant that can displace the electronic device in front of the individual, in the method, the electronic device is not hold by the individual but, instead, by a motorized support that can displace the electronic device in front of the individual, said motorized support being remotely controlled by the electronic device, the distance is computed in relation to a reference object of known size R and in physical relation to the individual and that is made part of the recorded images, the distance being computed with: COMPUTED DISTANCE=$R/(2*\arctan(S*F/2))$, where S is the size of the reference object in pixels in the image and F is the projection ratio, the reference object is selected from an object added on purpose, i.e. a rule or a credit card, or from an object that is part of the individual, i.e. a pair of glasses worn by the individual, a distance between his/her two eyes, his/her pupil(s) size(s), the computed distance that is kept as being the measured limit distance is an average of two computed distances, an up computed distance and a down computed distance, the up computed distance corresponding to the limit distance detected by the individual while the distance between his/her eyes and the electronic device increases starting with the electronic device closest as possible to his/her face, the down computed distance corresponding to the limit distance detected by the individual while the distance between his/her eyes and the electronic device decreases starting with the electronic device farthest as possible to his/her face, the input interface 4 receiving from the individual an entry corresponding to the detection by the individual of the related limit distance for each of the increase and decrease of the distance, the computation circuits computes from the recorded images the distance between the eyes of the individual and the electronic device continuously or semi-continuously and the computation circuits changes the size of the displayed at least one predetermined symbol according to the computed distances in order to have a constant angular size of the displayed at least one predetermined symbol, the measured limit distance is an average of a number of computed distances of detection obtained by repeating the displacements of the electronic device in front of the individual, the down computed distance is obtained and computed before the up computed distance, the computation circuits computes from the recorded images the distance between the eyes of the individual and the electronic device only when the input interface 4 receives from the individual an entry corresponding to the detection by the individual of the limit distance, the computation circuits computes from the recorded images the distances between the eyes of the individual and the electronic device continuously, practically at a maximum rate allowed by the electronic device imaging and processing capabilities, the computation circuits computes from the recorded images the distances between the eyes of the individual and the electronic device semi-continuously, at predefined intervals of time, and also when the input interface 4 receives from the individual an entry corresponding to the detection by the individual of the limit distance, the predefined intervals are equal during the method, the predefined intervals are variable during the method, the predefined intervals correspond to a maximum rate allowed by the electronic device imaging and processing capabilities, the computations of distances being then continuous, the computed distances between the eyes of the individual and the electronic device computed continuously or semi-continuously are used to determine the direction of displacement of the electronic device related to the face of the individual, the at least one predetermined symbol is selected from: characters, numerals, numbers, sentences of text, duochrome tests and images, the input interface 4 is configured to receive from the individual as the entry corresponding to the detection by the individual of the limit distance, an entry selected from: a push of a button of the electronic device, a release of a button of the electronic device, a voice input such as a vocal command or a reading, a mimic change of the face in the images, a rotation of the electronic device, the at least one predetermined symbol comprises at least one sentence of text or duochrome tests and the input interface 4 is configured to receive from the individual as the entry corresponding to the detection by the individual of the limit distance a voice input corresponding to the reading of said at least one sentence of text or of duochrome tests and the electronic device is further configured to compute the reading speed and as soon as the computed reading speed is modified to a predetermined amount, the computation circuits keeps the corresponding computed distance as being the limit distance, the input interface 4 is configured to receive from the individual as the entry corresponding to the detection by the individual of the limit distance a voice input, the electronic device is further configured to recognize specific words in the voice input, the electronic device is further configured to modify the at least one predetermined symbol displayed according to recognized words, the ratio of the size of the displayed at least one predetermined symbol to the computed distance is kept constant, the at least one predetermined symbol is/are from a near vision test requesting a detection by the individual, the near vision test is selected from Parinaud, Jaeger, ETDRS near tests or any other equivalent near test requesting a detection by the individual, the predetermined amount for the modification of the computed recognizing/reading speed is between 10% and 20%, the predetermined amount for the modification of the computed recognizing/reading speed is 15%, the button of the electronic device is a material or touch/sensitive one, the mimic change of the face in the images is selected from a prolonged closing of at least one eye, an opening of the mouth, a closing of the mouth, a rotation of the face, the value of visual correction for the near vision is expressed as an ADDITION in diopter that is computed with: ADDITION=$1/(NV)-1/(D)$, where NV is a near vision distance in length unit chosen for the individual and D is the measured limit distance, the ADDITION is further corrected by a comfort factor x according to: ADDITION=$1/(NV)-1/(D)+x$, where x is a comfort factor and is in diopter, the comfort factor is 0.25 diopter when 1/D<2 diopters, the comfort factor is 0.5 diopter when 1/D>=2 diopters.

The invention is also related to an electronic device that is the portable medium 1 used in the measurement method for determining a value of a visual correction need for near vision of an individual in a natural posture for near vision of the invention, said electronic device comprising at least a display screen 3, a mapping sensor 7, an input interface 4, and computation circuits with a microprocessor 9 executing a program according to the measurement method of the invention.

The invention is also related to a microprocessor program adapted to perform the measurement method of the invention when installed and executed in the described electronic device.

The invention is also related to a readable storage medium comprising the microprocessor program adapted to perform the measurement method of the invention. The readable storage medium can be read directly by the electronic device of the invention or read by an external computer 2 or server that transmits the microprocessor program to the electronic device of the invention. Microprocessor program is related to a program that can be executed in fine in a microprocessor but the program can be in machine language or in a higher programing language. The program is made of code instructions for performing the method of the invention.

BRIEF DESCRIPTION OF THE DRAWING FIGURE

The drawing FIGURE schematically illustrates an embodiment of the invention.

DETAILED DESCRIPTION OF EXAMPLE(S)

The following description will allow a good understanding of how the invention may be implemented.

In its general principle, the invention is related to a method to determine the ADDITION need for the near vision of an individual, the individual holding an electronic device for displaying a visual test, the individual having correction for far vision in the case he has impaired far vision. The individual changes the distance from his/her eyes to the electronic device, the addition being determined from a minimal distance from which the individual reach a minimum visual performance criteria. Different visual tests may be used: acuity chart, reading speed test, duochrome test . . . . The electronic device has distance determination means and a calibration step is implemented that can use different processes.

The following example is related to an individual having impairments both in far and near visions but it could be used with individuals only needing near vision correction. The near vision impairment is generally caused by presbyopia and is related to a refractive error in the eye.

Beforehand, a far vision correction is provided to the individual, for example using his/her current eyewear or using trial lens. The near vision test is conducted using an electronic device having a display to present visual tests to the individual. The correction needed, expressed here as an ADDITION is then determined from the visual performance of the individual for different distances between the individual and the electronic device: the distance(s) for which an acceptable near visual performance is obtained and/or ends according to the way the invention is executed, gives a measured limit distance D that is used to compute the ADDITION to provide. This method does not need any additional convex lens to conduct the determination of ADDITION for near vision contrary to known tests.

The invention then proposes to determine the ADDITION as a function of the direct or indirect measurement of the amplitude of accommodation AA of the individual using a portable medium 1 that is an electronic device such as a tablet or a smartphone or any equivalent mobile/portable electronic device. Typically, the electronic device comprises a display screen 3, an optical sensor 5, an input interface 4 and computation circuits with a microprocessor 9 executing a program.

The distance between the eyes of the individual and the electronic device is measured either directly if the electronic device has direct measuring means such as a telemeter means or indirectly, through computation of data acquired by the electronic device, data that can be images of the individual and that are analyzed. Note that the distance measurement can be done by entry of its value in the electronic device through voice recognition, for example an assistant with a scaled rule reading the distance on the scales rule. In fact, any means for getting the distance between the individual face or eyes can be used.

During the measure, preferably, the individual has a perfect far vision in terms of visual acuity with or without glasses (emmetropic subjects). The subject wears his optimal pair of glasses/spectacles for far vision (right and left eye and all possible corrections, in sphere, cylinder and axis) and this gives him a visual acuity for far vision of 10/10; 20/20, 6/6 or 0.0 LogMar corresponding to a perfect far vision, or better, according to the referential. This correction for far vision may be included in the current glasses of the individual or in trial glasses if a new correction for far vision has just been done.

This optimal pair for far vision do not provide any specific correction for near vision.

The benefits of having the subject wear his/her optimal pair of glasses for far vision are the following:

in case of high myopia/hyperopia, the distance between the punctum remotum (corresponding to the up distance or farthest distance) and the punctum proximum (corresponding to the down distance or closer distance) may be small. In this case, any distance measurement error can lead to inaccurracy when determining accommodation or addition need, and so would require very precise measuring device. For instance, for −4D myopic wearer, frequent situation in Asia, having 1D accommodation, if the subject do not wear his/her optimal pair of glasses for far vision, then punctum remotum is 250 mm beyond subject, and punctum proximum is 200 mm. A +/−10 mm measurement distance error would lead to 20% error on accommodation according to the following calculation: ($\Delta acc/acc \sim (10/200+10/250).acc \sim 0.2*acc$). If the subject wears his/her optimal pair of glasses, punctum remotum will be infinite while punctum proximum will be 1000 mm. In that case a 10 mm measurement distance error will lead to 1% error on accommodation: ($\Delta acc/acc \sim (10/1000+10/infinite) \sim 0.01*acc$.

If the subject has astigmatism and do not wear his/her optimal pair of glasses, it may be difficult to determine with accuracy the punctum proximum and so the limit distance D, since he/she will perceived blur whatever is the distance D.

As an indirect measurement of the amplitude of accommodation, it is proposed to measure a distance called measured limit distance D and at which the near vision quality of the individual changes, or, preferably, to measure two such distances that are at the most advanced point, PAA (corresponding to the down distance or closer distance), and at the farthest advanced point, PAF (corresponding to the up distance or farthest distance), where the individual can no more read, that is PAA point, or can now read, that is PAF point, predetermined test symbol(s) formed of letters or optotypes of a text displayed on the electronic device displaced in front of his/her eyes. In this preferred last case, the distance D which is considered here as being in relation to the amplitude of accommodation, is the average of those two measurements: average of PPA distance and PAF distance As we will see later, using D, the measured limit distance, it is possible to compute the ADDITION for each individual. This ADDITION can be computed as a minimum value and a further correction may be added to it.

Practically, the individual starts with the electronic device from a remote position, for example he/she holds the electronic device in front of him/her having stretched arms, and he/she approaches the display closer to his/her eyes until his/her visual performance decrease, practically where the individual can no more read, this last position being detected by the individual he/she then informs the electronic device with an entry in its input interface 4. Informed with this entry, the electronic device that measure the distance between the eyes and the electronic device, uses/keeps the corresponding distance as the measured limit distance D and can compute the ADDITION. This distance is also the down distance related to PAA point.

As previously mentioned, this can be done for both directions of displacement of the electronic object and, in such a case, the measured limit distance D is the average of the distances of the two detections for both directions of displacement of the electronic device. In such a case of averaging with PAA and PAF, the distance for PPA is obtained as mentioned above. The distance for PAF is obtained the following way: the electronic device is arranged at a very close distance of the individual, close distance at which the individual cannot see clearly/cannot read the test text, and the electronic object is then displaced further from the individual until the individual detects that he/she can now start to see clearly/read and thus have good visual performance, this detection gives the up distance. The measured limit distance D that is used to compute the ADDITION is then the average of the two distances down/PAA and up/PAF.

Different predetermined symbol(s) may be shown to the individual with the use of one of different tests to assess the performance and the quality of reading in near vision. A near test such as Parinaud, Jaeger, ETDRS . . . may be used. For example, the visual acuity VA of the individual in near vision may be assessed by asking him to gaze at one line of test text of the test, the one that is the best VA-1 line in the different line sizes, and then to approach this same line of text until he cannot read it anymore: the related distance between the eyes and the screen is then the measured limit distance or the near point forward PAA in the case an averaging is done between PAA and PAF for two directions of displacement of the screen obtained as mentioned above.

In a more advanced embodiment, a reading speed software (RSD) can be used for testing if the capacities of reading change in terms of gain or drop of reading speed and thus providing a detection that is indirect from the individual. Typically, with the reading speed software, the change of reading speed resulting in a detection of a change of reading capacity is about 15%.

Still in this more advanced embodiment with the reading speed software, the reading speed is continuously monitored when the subject approaches [or moves away] the electronic device with the test text until the patient cannot read it anymore or the reading speed decreases significantly [or can now read it or read it with a sufficient speed]: this gives the PAA point and thus the down distance [or the PAF point and thus the up distance]. This is done for the two possible directions of displacement of the electronic device and the measured limit distance D that is used to compute the ADDITION is then the average of the two down and up distances. The reading speed is thus determined automatically from voice recognition embedded in the electronic device, so that the individual do not have to provide any feedback for the measurements.

It may be noted that the direct detection by the individual (this is when the individual directly informs the electronic device of the detection of a change of his/her reading capacity with the entry he/she make in the electronic device), can be combined with the indirect detection (this is when the reading speed software automatically informs the electronic device of the detection of a change of the reading speed), to determine the measured limit distance D. For example an average could be made with the two distances obtained by direct input by the individual and by automated input by the reading speed software, possibly for each direction in case PAA et PAF points are considered. In this last case, each distance for a point, either PAA or PAF, is the result of an averaging of two distances. More generally, instead of using one unique criterion for the detection, for example direct input or reading speed, any combination of criteria may be used, the combination being an averaging of distances or a more complex decision rule.

The size of letters displayed with test such as Parinaud, Jaeger, on the electronic device will be calculated so as to have a constant angular size at any time/distance of measurement. This means that the ratio letter size/distance may be globally constant for the range of distance used.

Others near vision tests may be used and for example with a predetermined symbol shown in the form of a duochrome test, the individual being asked to move the test closer to get PAA and thus the down distance, and then, after the down distance has been detected, to move it further to get PAF and thus the up distance, and to finally get D as an average, for each direction the detection corresponding to the position where the display is perceived with similar contrast between red and green test. It is possible to get D as one measurement of distance in asking the individual to displace down the electronic device from position to position and to move it up and down on short range around each new down position to detect the position where for each direction of the short range moves, the display is perceived with similar contrast between red and green test.

It is also possible to configure the electronic device to manage automatically the direction of displacement of the electronic device and/or the start distance for its displacement as a function of the visual performance that can be estimated. For instance, when using reading speed software and/or duochrome test, reading speed software is used to check if there is change in reading speed or voice recognition is used to detect if the individual says red or green for the most dominant color. If there is no fall of reading speed compared to previous reading speeds or if the individual says green, the distance must be get shorter, and the electronic device instructs the individual to move closer the electronic device. The electronic device can also check that the new distance is correct given the previous one and the instructions given, thanks to the distance measuring means of the electronic device.

For the displacements, the electronic device is preferably handed by the individual himself, to perform the measurement in natural reading position, but in case the expected distance(s) for PAA and possibly PAF [PAA only in the case it is considered only one direction of displacement and PAA and PAF in the case it is considered an average with two directions of displacement] is longer than individual's upper limbs, the electronic device can be placed on a fixed support and this is the individual that moves or the electronic device can be handed by an assistant. This is the same when it is not possible to get D because at the maximum distance with the upper limbs of the individual, the vision is already too poor or impossible. If the distance is very important, a minimum ADDITION can be chosen: for instance, if PAA or PAF is 1 m or above (farther from the individual), accommodation of the individual is less than 1 diopter, and in such a case it is recommended to provide him/her an ADDITION >=2 diopters.

The distance between the electronic device and the face or better the eyes of the individual can be measured in different ways. It is preferred an automatic measurement resulting from a computation of images of the individual obtained with the frontal camera—on the side of the display screen 3 that is shown at the individual—of the electronic device that can be a smartphone. In this case, a two-step process is considered.

The first step, before the electronic device displaying a visual test is displaced in front of the individual, is a calibration step. This is for the determination of the projection ratio F in degrees per pixel (°/pix) of the camera (that is an equivalent of the focal length for single lens reflex). A very simple technique is to aim at a far object, then record a panorama video by oscillating or rotating the smartphone, roll and pitch movements, while acquiring data from the embedded inertial motion unit 8 of the smart phone. Then, image processing can quantifies the displacement P in pixels of that far object in the video and the corresponding angular rotation A can be measured with signal processing of the inertial motion unit data. The projection ratio of the camera F is the ratio F=A/P.

The projection ratio can be calculated for only two different instants, possibly with averages, on an oscillating or rotating period, where the inertial motion unit data is accurate and the related image is sharp enough. The error of the model, caused by a not far enough object or a not pure enough rotation of the electronic device can be checked by computation of the related standard deviation. Of course, such technique can be used on stable earth ground without problem. This is not the same if such technique is used in an airplane, on a boat or other moving environment, and caution must be taken in these instances.

A more sophisticated model of the camera can be used, including focus and radial distortion or other complex piecewise polynomial interpolation. A good calibration should be made in the same conditions as that for measurements, notably with same framing.

Other calibration processes are possible. For instance, it is possible to take a picture with the electronic device of a reference object of known size at a known distance. The calculation of the angular size A of the object and its size P in pixels in the image for computing F=A/P are then relatively simple.

The second step is the distance measurement that is mainly done when the electronic device displaying a visual test is displaced in front of the individual for assessing his/her near vision. If the electronic device has a measuring means such as a telemeter, the distance can be directly obtained. In the more general cases, the measured distance is computed and preferably from images taken by the electronic device. For this, a reference object with a known real size R in mm (or another length unit) must be included in the images of the individual. The reference object can be an object added on purpose or an object pertaining to the individual. The reference object can be scaled with marks or not. Using a scaled reference object makes possible the electronic object to get directly in the image the real size of the object in length unit instead of having to input it. For example this can be the interpupillary distance (obtained from a pupillometer or through the use of a scale with scale marks arranged horizontally above or under the eyes of the individual and which image is analyzed), this can be the size of the worn/carried glasses (from reference or scan) or the diameter of the lens of a trial frame (with the strong advantage that the large diameter of its elliptic image is independent of its orientation) or a scale with scale marks arranged horizontally above or under the eyes of the individual. The reference object can thus be added on purpose and is for example a rule or a credit card. The reference object is an element of known size, notably as having been measured previously, preferably pertaining to the individual, and is for example a pair of glasses, the distance between the eyes of the individual, a pupil.

More generally, other reference objects can be used in the images, as an additional clip set on the frame of the glasses (for example a scale with scale marks), a credit card near the face, the size of the outer bounding of the iris, another anthropometric data. Then, an image of the individual with the reference object is taken. The said size of the reference object in pixel, S, is extracted by image processing.

Knowing the projection ratio F, the distance D can be calculated according to the following formula: D=R/(2*ARCTAN(S*F/2)) where R is the real size in length unit of the object and S the said size in the image in pixels.

This formula can be approximated to: 180*R/(pi.S.F), where pi=3.1415926, said approximation being valid if S*F is small.

With a relevant program in the electronic device, if the image processing is impossible, the individual is informed that the distant measurement is not possible. If solutions to the problem are identified by the program/software of the electronic device, for example because the image was taken facing directly the sun or a strong source of light, those solutions can be provided to the individual by the electronic device.

In a more advanced embodiment, those two steps can be done almost simultaneously, by using the reference object to calibrate the projection ratio F and for the computations of the distances.

For instance, the following text "Rotate you phone as you do with your head to say no, as soon as you can read this text", then, when the individual rotate his phone, the maximum reading distance has been reached, and the camera calibration can be done together with distance computation.

Note that, if the electronic device has a 3D scanner, the distance can be extracted from Z map of the image data. Of course, the distance can be directly measured with a measuring tape or any other specific distance measuring mean.

For the tests to be accurate, it is important that the real size of the visual test be correctly defined so that to provide correct angular size of the visual test when assessing the visual acuity for instance. For that purpose, it is preferred to get the real size of the display screen 3 and the number of pixels of said display screen 3 from known characteristics of the model of the electronic device. This can be achieved using a database storing characteristics of useable electronic devices and to query the database for the electronic device currently used. If this is not possible, a direct calibration by an eye care professional or the individual may be still possible. For example, the eye care professional or the individual can apply a rule or a flat object of know dimension such as a credit card on the screen, and then on the obtained image move sliders, a reticule or a cursor displayed by a program of the electronic device until both coincide. Then, the size of the screen can be deduced.

In the same way, the size of the test can be corrected from the distortion of the lenses worn by the individual. For instance, if the individual is myopic and the distance between his/her eyes and the lenses is important (a fortiori for trial frame), then the test can be magnified of a determined factor.

Finally, knowing the limit distance D, the ADDITION related to the value of the visual correction need can be computed.

When the measured limit distance D is obtained for the test used, for instance the distance giving same contrast for red/Green test or giving 10/10 acuity, the ADDITION can be computed with the following formulae:

ADDITION=2.5−1/D+x in case the near vision distance is 40 cm,

ADDITION=3.0−1/D+x in case the near vision distance is 33 cm,

Parameter x is an extra value provided to the individual so that it gives him/her visual comfort and the capacity to see clearly for shorter distance, and so that he/she does not need to use full accommodation to see clearly in near vision. Parameter x that is a comfort factor, is preferably 0.25 diopter when 1/D<2 diopters or 0.5 diopter when 1/D>2 diopters and in any cases, it should not be more than 0.5 diopter.

Other formulae may also be used and for example a more general one:

ADDITION=1/NV−1/D+x, where NV is a near vision distance in length unit that has been chosen for the individual.

It has to be noted that ADDITION is a positive value, so if the formula gives a negative value, no addition is provided.

It should be understood that the determination of the needed additional correction for near vision is preferably done for each eye individually and that the described processes should then be repeated for each eye. Moreover, as the proposed method can be made totally automated and executed by the individual solely, it can be repeated with same tests and/or different tests and the results averaged to get accurate results. Additional checks can be implemented in the executed program of the electronic device in order to detect incoherencies between measurements, inputs, results, etc. With sufficient processing power, it is possible to do the process continuously or almost continuously on a video stream of images instead of individual images taken at specific moments.

Note also that, in the example given, this is the electronic device computing means that is executing a program giving the needed ADDITIONAL correction. It should be understood that in case the electronic device has communication means for exchanging data with an external, possibly remote, computer or server, for example through TCP/IP or telephone network, part of the program can be executed in the computer or server. For example, images of the face of the individual can be sent to a remote computer for computing the distance from the image and/or the final computation of the ADDITION can be done in this remote computer. This could be useful because the external computer 2 or server has greater computing capabilities than the electronic device that is a mobile/portable device and, also, because the external computer 2 can have access to additional data that can be used, for example previous correction for the individual and statistical information related to the vision of a population to which the individual can be assimilated, in order to set-up additional coherency checks in the process.

The invention claimed is:

1. A measurement method for determining a value of a visual correction need for near vision of an individual for near vision wherein a recognizing limit distance is determined so that the individual is able to recognize at least one predetermined symbol disposed farther than said recognizing limit distance relatively to the individual and unable to recognize said at least one predetermined symbol disposed closer to the individual than said recognizing limit distance, the method comprising steps of:

displaying a portable medium configured to display said at least one predetermined symbol in front of a face and eyes of the individual to change a frontal distance between his/her eyes and the portable medium, when the recognizing limit distance is detected by the individual, measuring said detected recognizing limit distance and determining the value of the visual correction need from said measured detected recognizing limit distance, wherein said visual correction need comprises an accommodation compensation need, and wherein the portable medium is an electronic device comprising at least a display screen, an optical sensor and an input interface, designed to perform that:

the display screen displays the at least one predetermined symbol, the optical sensor records images of the face of the individual, at least while a distance between his/her eyes and the electronic device changes, a computed distance between the eyes of the individual and the electronic device is computed from the images, and when the input interface receives from the individual an entry corresponding to the detection by the individual of the recognizing limit distance, a corresponding computed distance is kept as being the measured detected recognizing limit distance and used to compute the value of the visual correction need, and wherein the value of the visual correction need for the near vision is expressed as an ADDITION in diopter that is computed with:

ADDITION=1/(NV)−1/(D)

where NV is a near vision distance in length unit chosen for the individual and D is the measured detected recognizing limit distance.

2. The measurement method according to claim 1, wherein the electronic device further comprises computation circuits with a microprocessor executing a program, the portable medium being designed to measure that at least the value of the visual correction need is computed by the computation circuits within the portable medium.

3. The measurement method according to claim 1, wherein the electronic device further comprises a data communication interface for exchanging data to and from an external computer, the portable medium and the external computer being designed to measure that at least the value of the visual correction need is computed by the external computer.

4. The measurement method according to claim 1, wherein the individual has an impaired far vision and wherein the individual is wearing a pair of glasses correcting his/her impaired far vision.

5. The measurement method according to claim 1, wherein the individual has a perfect far vision and wherein the individual is not wearing a pair of glasses.

6. The measurement method according to claim 1, wherein, in an initial step of the method, before the electronic device is displaced to change the distance between the eyes and the electronic device, the electronic device is calibrated to determine a projection ratio F in degrees per pixel.

7. The measurement method according to claim 6, wherein, in an initial step of the method, before the electronic device is displaced to change the distance between the eyes and the electronic device, the electronic device is calibrated to determine the projection ratio F in degrees per pixel using a reference object of known size that is arranged to be imaged in the recorded images.

8. The measurement method according to claim 1, wherein the computed distance that is kept as being the measured detected recognizing limit distance is an average of two computed distances, an up computed distance and a down computed distance, the up computed distance corresponding to the recognizing limit distance detected by the individual while the distance between his/her eyes and the electronic device increases starting with the electronic device closest to his/her face, the down computed distance corresponding to the recognizing limit distance detected by the individual while the distance between his/her eyes and the electronic device decreases starting with the electronic device farthest to his/her face, the input interface receiving from the individual an entry corresponding to the detection by the individual of the related recognizing limit distance for each of the increase and decrease of the distance.

9. The measurement method according to claim 1, wherein the at least one predetermined symbol is selected from: characters, numerals, numbers, sentences of text, duochrome tests and images and wherein the electronic device is a smartphone or a tablet or a portable computer.

10. The measurement method according to claim 1, wherein the input interface is configured to receive from the individual as the entry corresponding to the detection by the individual of the recognizing limit distance, an entry selected from: a push of a button of the electronic device, a release of a button of the electronic device, a voice input, a change in the visual expression of the face in the images, a rotation of the electronic device.

11. The measurement method according to claim 10, wherein the change in the visual expression of the face in the images is selected from a prolonged closing of at least one eye, an opening of the mouth, a closing of the mouth, and a rotation of the face.

12. Electronic device that is a portable medium for determining a value of a visual correction need for near vision of an individual for near vision, said electronic device comprising at least a display screen, a mapping sensor, an input interface, and computation circuits with a microprocessor executing a program according to the measurement method of claim 1.

13. A non-transitory computer-readable medium on which is stored a microprocessor program adapted to perform the measurement method of claim 1 when installed and executed in an electronic device that is a portable medium for determining a value of a visual correction need for near vision of an individual for near vision, said electronic device comprising at least a display screen, a mapping sensor, an input interface, and computation circuits with a microprocessor.

14. The measurement method according to claim 1, wherein, in an initial step of the method, before the electronic device is displaced to change the distance between the eyes and the electronic device, the electronic device is calibrated to determine a projection ratio F in degrees per pixel, and the electronic device further comprises an inertial motion unit for recording motions of the electronic device, the determination of the projection ratio F is done by oscillating with rotation the electronic device and computation of recorded motions with reference to recorded related images from the optical sensor of the electronic device to quantify the displacement P in pixels of an object in the recorded images and the corresponding angular rotation A of said object, F being computed with $F=A/P$.

* * * * *